United States Patent [19]  
Malhotra et al.

[11] Patent Number: 4,931,452  
[45] Date of Patent: Jun. 5, 1990

[54] N-CYANOMETHYL-2-PYRIDINONE INSECTICIDES

[75] Inventors: Sudarshan K. Malhotra, Walnut Creek; James E. Dripps; Gregory A. Bradfisch, both of Concord; Susan Wollowitz, Walnut Creek, all of Calif.; Ingrid L. Knox, Midland, Mich.

[73] Assignee: The Dow Chemical Company, Midland, Mich.

[21] Appl. No.: 237,014

[22] Filed: Aug. 24, 1988

Related U.S. Application Data

[63] Continuation-in-part of Ser. No. 119,113, Nov. 10, 1987, abandoned.

[51] Int. Cl.$^5$ .................. A01N 43/40; C07D 211/78; C07D 211/72; C07D 211/84
[52] U.S. Cl. ..................................... 514/344; 546/287; 546/291; 546/292; 546/296; 546/297; 546/298; 546/300; 514/345; 514/346; 514/348; 514/349; 514/350; 514/351
[58] Field of Search ............... 546/287, 291, 292, 296, 546/297, 298, 300; 514/344, 345, 346, 348, 349, 350, 351

[56] References Cited

U.S. PATENT DOCUMENTS 3,682,936 8/1972 Tarba.

FOREIGN PATENT DOCUMENTS

| 216541A | 1/1987 | European Pat. Off. | 546/300 |
| 6038363 | 8/1983 | Japan | 546/300 |
| 61-72754 | 4/1986 | Japan | 546/300 |
| 61-186363 | 8/1986 | Japan | 546/300 |

OTHER PUBLICATIONS

Abramovitch, *Pyridine and its Derivatives*, Supplement Part 3 (1974), pp. 745–752.

Primary Examiner—Mary C. Lee  
Assistant Examiner—Robert C. Whittenbaugh  
Attorney, Agent, or Firm—D. Wendell Osborne

[57] ABSTRACT

Substituted N-cyanomethyl-2-pyridinones were prepared by the reaction of alkali metal substituted-2-pyridinates with monohaloacetonitriles and found to possess insecticidal properties. The alkali metal substituted-2-pyridinates can be preformed or prepared from the corresponding 2-halopyridines or 2-pyridinols in the reaction medium. N-cyanomethyl-3-fluoro-5-(trifluoromethyl)-2-pyridinone, for example, was prepared from 2,3-difluoro-5-(trifluoromethyl)pyridine and found to control aster leafhoppers both on contact and systemically.

39 Claims, No Drawings

N-CYANOMETHYL-2-PYRIDINONE INSECTICIDES

CROSS-REFERENCE TO RELATED APPLICATION

This application is a continuation-in-part of Application Ser. No. 119,113, filed Nov. 10, 1987 now abandoned.

BACKGROUND OF THE INVENTION

The present invention relates to novel pyridinone compounds and their use in controlling insects.

The control of insects is critically important in the production of food and fiber and the protection of the public health. New classes of chemicals that are useful in providing insect control are intensively sought and, when found, highly prized.

Certain substituted N-pyridinyl-2-pyridinone compounds and substituted N-phenyl-2-pyridinone compounds have been disclosed to be insecticidal. Further, certain substituted 2-pyridinols (2-pyridinones) are known to be insecticidal and to protect wood from attack by insects.

SUMMARY OF THE INVENTION

It has now been found that N-cyanomethyl-2-pyridinones are useful in controlling insects. In particular, compounds of Formula I

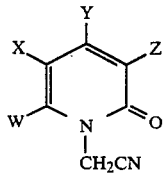

Formula I wherein
W represents H, F, Cl, CH$_3$, or CF$_3$;
X represents H, F, Cl, Br, I, R, OR, OPh, SR, CF$_2$Cl, CN, COR, C$_2$R', or CONR'R':
Y represents H, R, OR, SR, OR, or OPh:
Z represents H, F, Cl, Br, I, R, OR, SR, OPh, NO$_2$, or CN;
R represents C$_1$–C$_3$ alkyl or C$_1$–C$_3$ alkyl partially or totally substituted with fluorine;
R' represents C$_1$–C$_4$ alkyl;
with the proviso that at least one of W, X, Y, and Z represents other than H
are novel and control insects when applied to the insects or their locus or to plants upon which insects feed. The compounds are usually applied as components of an insecticidal composition containing an effective amount of at least one such compound in mixture with an agriculturally acceptable carrier.

The present compounds can be prepared by combining an appropriately substituted 2-pyridinol of Formula II

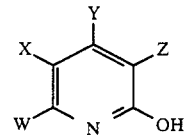

Formula II wherein W, X, Y, and Z are as defined hereinabove and a base capable of abstracting a proton from a 2-pyridinol, or a preformed salt of a 2-pyridinol of Formula II and a base, with monochloroacetonitrile or monobromoacetonitrile in a solvent under conditions conducive to N-alkylation.

Alternately, the compounds can generally be prepared by combining a 2- or 6-halopyridine of Formula III

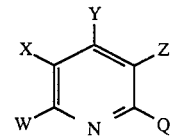

Formula III wherein Q represents F, Cl, or Br and W. X, Y, and Z are as defined hereinabove with an alkali metal hydroxide in a solvent under conditions conducive to the formation of an alkali metal salt of a substituted 2-pyridinol of Formula 11 and combining this intermediate, without isolation, with monochloroacetonitrile or monobromoacetonitrile under conditions conducive to the formation of the desired novel insecticides of the invention. The desired products can be recovered by conventional means. This process, of course, works best where W does not represent F or Cl because of competing reactions which reduce the yield.

DETAILED DESCRIPTION OF THE INVENTION

N-cyanomethyl-2-pyridinone compounds containing fluoro, chloro, bromo, iodo, chlorodifluoromethyl, phenoxy, nitro, cyano, alkoxycarbonyl, dialkylcarbamoyl, and optionally fluorinated alkyl, alkoxy, alkylthio and acyl substituents as described in the Summary of the Invention (compounds of Formula 1 containing designated substituents W, X, Y, and Z) are the compounds of this invention. Those N-cyanomethyl-2-pyridinone compounds of Formula I wherein W represents H, or wherein X represents Cl, Br, I, CF$_3$, CF$_2$H, C$_2$F$_5$, CN, or (C$_1$–C$_4$ alkoxy)carbonyl, or wherein Y represents H, or wherein Z represents H, F, Cl, or CN are preferred. Compounds possessing a substituent indicated to be preferred at each of positions W, X, Y, and Z are more preferred. Substituted N-cyanomethyl-2-pyridinones of Formula 1 wherein X represents trifluoromethyl are especially preferred and those wherein W represents hydrogen, X represents trifluoromethyl, Y represents hydrogen, and Z represents hydrogen, fluoro, chloro or cyano are more especially preferred.

The compounds, N-cyanomethyl-3-fluoro-5-(trifluoromethyl)2-pyridine, N-cyanomethyl-3-chloro-5-(trifluoromethyl)pyridine, and N-cyanomethyl-3-cyano-5-(trifluoromethyl)pyridine are most especially preferred.

The compounds of the present invention can be prepared by the reaction of an appropriately substituted 2-pyridinol of Formula II and a base capable of abstracting a proton from said 2-pyridinol, or a preformed salt of said 2-pyridinol and said base, with a monohaloacetonitrile (monochloroacetonitrile or monobromoacetonitrile). The reaction is carried out in water or in an organic solvent and under conditions leading to N-alkylation. Typically, the pyridinol, base and monohaloacetonitrile are combined in a solvent and the mixture is agitated and allowed to react at moderate temperatures until a substantial fraction of the 2-pyridinol of Formula 11 has reacted or until a recoverable amount of the substituted N-cyanomethyl-2-pyridinone of Formula I has formed.

Suitable bases are those that form salts with 2-pyridinols, but do not react substantially with monohaloacetonitriles when properly employed in the process. Alkali metal hydroxides and carbonates are typical. Bases which are somewhat reactive with monohaloacetonitriles are used in only approximately equimolar or smaller quantities relative to the substituted 2-pyridinols of Formula II or are used to prepare preformed salts of 2-pyridinols. Bases which are relatively unreactive can be used in excess. For laboratory procedures an excess of potassium carbonate is convenient.

The monohaloacetonitrile and substituted 2-pyridinol are usually employed in approximately equimolar amounts although an excess of one or the other can be used. It is often helpful to employ a small excess of the monohaloacetonitrile to ensure complete reaction of the substituted 2-pyridinol and, thereby, to conserve this starting material.

Either water or an organic solvent or mixtures thereof can be employed as the reaction medium. When water is employed, it is usually helpful to add a phase transfer catalyst, such as benzyltrimethylammonium chloride. Organic solvents which are unreactive under the reaction conditions are suitable. Those in which substituted 2-pyridinol salts have some solubility, are preferred. These include dimethylsulfoxide, tetramethylene sulfone, N,N-dimethylformamide, N-methylpyrrolidone, acetonitrile, acetone, methyl isobutyl ketone, diglyme, and 2-propanol. Dipolar aprotic solvents are often preferred, especially when W represents hydrogen. When W represents fluoro, chloro, or trifluoromethyl, alcohols and ketones are often preferred.

The reaction proceeds smoothly at ambient temperatures and at these temperatures requires about 15 min. to about a day. Temperatures of about $-20°$ C. to about $150°$ C. are typical: temperatures of about $0°$ C. to about $120°$ C. are preferred, and temperatures of about $20°$ C. to about $100°$ C. are especially preferred. A broad range of pressures can be employed as pressure has little influence on the process.

The N-cyanomethyl-2-pyridinone product of Formula I can be recovered from the reaction mixture of the process by conventional means. Water is often added, if not already present, to dissolve the byproduct halide salt. When water-soluble solvents are employed, the addition of water usually causes the crude product to precipitate as a solid, which can be recovered by filtration and drying. If water is not added the insoluble by-products are typically removed by filtration and the volatiles are removed by evaporation to obtain the desired product in impure form. Crude products recovered as above can be further purified by conventional means, such as recrystallization from a solvent, such as methanol, toluene, 1,1,1-trichloroethane, and the like. The purified products are crystalline solids.

It must be noted that, since the anions derived from the 2-pyridinols of Formula 11 are ambient anions, two different alkylation products are possible, N-alkyl-2-pyridinones and 2-alkoxypyridines. Bulky substituents in the 3-position (Z) favor N-alkylation whereas bulky substituents in the 6-position (W) favor O-alkylation. Pyridinate anions unsubstituted in the 6-position (W represents hydrogen) generally give a preponderance of N-alkylation products. N-alkylation is generally favored by alcohol and ketone solvents. A discussion of 0 vs N-alkylation of 2-pyridinols is presented in Abramovitch, *Pyridine and its Derivatives*, Supplement Part 3, (1974), pp 745–752.

The requisite substituted 2-pyridinol starting materials of Formula 11, which are tautomeric with and functionally equivalent to 2-pyridinones, are known in the art or can be prepared by methods described in the art. They are typically prepared by hydrolysis of an appropriate compound of Formula III, which compounds are also well known in the art or can be prepared by methods described in the art.

2-Pyridinol starting materials for the compounds of the present invention are also often conveniently prepared by demethylation or debenzylation of appropriately substituted 2-methoxy- and 2-benzyloxypyridines. This can be accomplished by treatment with concentrated aqueous hydrobromic acid or with iodo-trimethylsilane at ambient temperatures. The appropriately substituted 2-methoxy and 2-benzyloxypyridines are known in the art or can be prepared by methods known in the art. Many 2-methoxypyridines having substituents in the 3-position or the 5-position and optionally in other positions are conveniently prepared by lithiation of the correspondingly substituted 3-bromo-2-methoxypyridine or 5-bromo-2-methoxypyridine with an alkyl lithium reagent, such as butyl lithium, at low temperatures followed by treatment with an electrophilic reagent at low temperatures. In this way, for example, 3-(or 5-)alkyl substituted compounds can be made using alkyl iodides, 3-(or 5-)formyl compounds can be make using dialkylformamides, 3-(or 5-)alkylthio compounds can be made using dialkyl disulfides, and 3-(or 5-)hydroxy compounds can be made using trimethyl borate and hydrogen peroxide.

It is often convenient to hydrolyze a compound of Formula III with an alkali metal hydroxide in a solvent under conditions conducive to the formation of an alkali metal salt of a substituted 2-pyridinol of Formula II and to combine the mixture obtained (a mixture comprising a salt of a compound of Formula II and a solvent), without recovery of the 2-pyridinate salt, with a monohaloacetonitrile under conditions conducive to the formation of a substituted N-cyanomethyl-2-pyridinone compound of Formula I. Conditions conducive to hydrolysis (first step in the process) are well known in the art and conditions conducive to alkylation (second step in the process) are described in detail hereinabove for the identical alkylation using a substituted 2-pyridinol obtained independently.

Many of the substituted N-cyanomethyl-2-pyridinones of Formula I are useful as intermediates for the preparation of other substituted N-cyanomethyl-2-pyridinones of Formula I. Thus, compounds wherein X and/or Z represent hydrogen can be converted to the corresponding compounds wherein X and/or Z represent chloro or bromo by halogenation under conditions described in the art for N-methyl-2-pyridinones. Compounds wherein Z represents chloro or bromo can be converted to corresponding compounds wherein Z represents fluoro, alkoxy, alkylthio, or phenoxy by treatment with potassium fluoride, sodium alkoxide, sodium alkylthiolate, or potassium phenoxide, respectively, in a dipolar aprotic solvent such as dimethyl sulfoxide or N-methylpyrrolidone.

While it is possible to utilize the substituted N-cyanomethyl-2-pyridinones of Formula I directly as insecticides, it is preferable to use them in mixtures containing an insecticidally effective amount of the compound in combination with at least one agriculturally acceptable adjuvant or carrier. Suitable adjuvants or carriers should not be phytotoxic to valuable crops, particularly at the concentrations employed in applying the compositions for insect control in the presence of crops, and should not react chemically with compounds of Formula I or other composition ingredients. Such mixtures can be designed for application directly to insects or their locus or to plants upon which insects feed or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the insecticidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate alkylarylsulfonate salts, such as calcium dodecylbenzenesulfonate: alkylphenol-alkylene oxide addition products, such as nonylphenol-$C_{18}$ ethoxylate: alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate: dialkyl esters of sulfosuccinate salts, such as sodium di(2-ethylhexyl) sulfosuccinate; sorbitol esters, such as sorbitol oleate; quaternary amines, such as lauryl trimethylammonium chloride: polyethylene glycol esters of fatty acids, such as polyethylene glycol stearate; block copolymers of ethylene oxide and propylene oxide: and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorant, penetration aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with solid, particulate fertilizer carriers such as ammonium nitrate, urea and the like or with liquid fertilizers.

The concentration of the active ingredients in the insecticidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to insects, or their locus, or to plants upon which insects feed, generally contain about 0.001 to about 5 weight percent active ingredient and preferably contain about 0.01 to about 1.0 percent.

The present compositions can be applied by the use of conventional ground or aerial dusters and sprayers, by addition to irrigation water, and by other conventional means known to those skilled in the art.

The substituted N-cyanomethyl-2-pyridinones of Formula I are insecticides and acaricides having both contact and plant systemic activity. A variety of insects and mites including tobacco budworms, leafhoppers, planthoppers, aphids and whiteflies can be at least partially controlled. The compounds are particularly useful in preventing insect damage to valuable crop plants, such as rice, corn, wheat, sugar cane, cotton, potatoes, tobacco, soybeans, apples, peaches, and oranges. Their use to protect rice is preferred. The compounds can be applied directly to the insects or their locus or can be applied to the foliage or the root zone of plants upon which insects feed. Generally, their application to the foliage or the root zone (the soil in which the plant is grown) is preferred, in which case the compounds generally function as plant systemic insecticides.

The compounds of the present invention are applied in amounts sufficient to kill a large fraction of the insects present or invading the treated area within a reasonable time. The actual amount applied will vary depending on factors such as, the compound of Formula I selected, the insecticidal composition employed, the insect or mite to be controlled, the severity of the insect or mite infestation, the degree of control desired; whether contact or systemic activity is desired, the type of applicator employed, and the climatic conditions at the time of application. Application rates of about 1 g to about 10 Kg per hectare are typical; rates of about 10 g to about 1 Kg per hectare are preferred for the more active compounds.

The following examples are presented to illustrate the invention and should not be construed as limiting the scope.

EXAMPLE 1

Preparation of
N-Cyanomethyl-3-Chloro-5-(trifluoromethyl)-2-pyridinone

A mixture of 4.0 g (0.02 mole) of 3-chloro-5-(trifluoromethyl)-2-pyridinol, 2.6 g (0.022 mole) of monobromoacetonitrile, and 4.0 g of potassium carbonate in 40 ml of dimethyl sulfoxide was prepared and stirred at ambient temperature for 3 hours. Water was then added and the light brown solid that formed was separated by filtration and dried to obtain 2.3 g (45 percent of theory) of the title compound: melting point, 84°–85° C. This product had infrared and nmr spectra compatible with the assigned structure.

Anal.: Calc for $C_8H_4ClF_3N_2O$ &C, 40.59; % H, 1.69; %N, 11.84. Found % C, 40.46; % H, 1.56; %N, 11.79.

The following compounds were prepared similarly and found to have compatible elemental (C,H,N) analyses and nmr spectra;

N-cyanomethyl-3-fluoro-5-(trifluoromethyl)-2-pyridinon: mp, 142°–143° C.;
N-cyanomethyl-3-bromo-5-(trifluoromethyl)-2-pyridinone: mp, 76°–78° C.;
N-cyanomethyl-3-iodo-5-(trifluoromethyl)-2-pyridinone: mp, 100°–102° C.;
N-cyanomethyl-3-methyl-5-(trifluoromethyl)-2-pyridinone: mp, 73°–75° C.;
N-cyanomethyl-3-methoxy-5-(trifluoromethyl)-2-pyridinone: mp, 122°–124° C.;
N-cyanomethyl-3-phenoxy-5-(trifluoromethyl)-2-pyridinone: mp, 88°–91° C.:
N-cyanomethyl-3-cyano-5-(trifluoromethyl)-2-pyridinone: mp, 124°–126° C;
N-cyanomethyl-5-bromo-4-(trifluoromethyl)-2-pyridinone: bp, 180°–190° C. at 15–25 mm Hg:
N-cyanomethyl-5-chloro-3-fluoro-2-pyridinone: mp, 120°–122° C.;
N-cyanomethyl-5-chloro-3-fluoro-4-phenoxy-2-pyridinone: mp, 101°–103° C.;
N-cyanomethyl-5-iodo-3-fluoro-2-pyridinone: mp, 175°–176° C.;
N-cyanomethyl-3,5-dichloro-2-pyridinone: mp, 117°–119° C.:
N-cyanomethyl-5-(trifluoromethyl)-2-pyridinone: mp, 124°–126° C.;
N-cyanomethyl-3,5-dibromo-2-pyridinone: mp, 150°–151° C.:
N-cyanomethyl-5-bromo-3-fluoro-2-pyridinone: mp, 119°–121° C.:
N-cyanomethyl-5-chloro-2-pyridinone: mp, 99°–100° C.;
N-cyanomethyl-5-bromo-2-pyridinone: mp, 103°–105° C.;
N-cyanomethyl-3-bromo-2-pyridinone: mp, 171°–172.5° C.;
N-cyanomethyl-3-fluoro-2-pyridinone: mp, 126°–127° C.;
N-cyanomethyl-5-methyl-2-pyridinone: liquid;
N-cyanomethyl-5-methyl-3-fluoro-2-pyridinone: mp, 146–147.5° C.:
N-cyanomethyl-5-chloro-4-(trifluoromethyl)-2-pyridinone: mp, 86°–88° C.;
N-cyanomethyl-3-methylthio-5-(trifluoromethyl)-2-pyridinone: mp, 132°–135° C.:
N-cyanomethyl-5-methylthio-3-fluoro-2-pyridinone: mp, 80.5°–81.5° C.;
N-cyanomethyl-3-cyano-2-pyridinone: mp, 180–182° C.: N-cyanomethyl-3,5-difluoro-4-phenoxy-2-pyridinone: bp,
N-cyanomethyl-3,5-difluoro-4-phenoxy-2-pyridinone: bp, 220°–230° C. at 15–25 mm Hg:
N-cyanomethyl-5-methoxycarbonyl-3-fluoro-2-pyridinone: mp, 122–123° C.;
N-cyanomethyl-5-ethoxycarbonyl-3-fluoro-2-pyridinone: mp, 93.5–94.5° C.;
N-cyanomethyl-5-(1-methylethoxy)carbonyl-3-fluoro-2-pyridinone: mp, 107–109° C.;
N-cyanomethyl-5-(2-methylpropoxy)carbonyl-3-fluoro-2-pyridinone: mp, 80–81° C.;
N-cyanomethyl-5-cyano-3-chloro-2-pyridinone: mp, 173–175° C.;
N-cyanomethyl-5-cyano-3-fluoro-2-pyridinone: solid;
N-cyanomethyl-5-bromo-3-cyano-2-pyridinone: mp, 158–162° C.;
N-cyanomethyl-4-methoxy-3-cyano-2-pyridinone: mp, 188–191° C.;
N-cyanomethyl-5-acetyl-3-cyano-6-methyl-2-pyridinone: mp, 128–129.5° C.; and
N-cyanomethyl-3,5,6-trichloro-2-pyridinone: mp, 173–174° C.

Other compounds which can be prepared by this general method, using the teachings herein, include the following: N-cyanomethyl-6-fluoro-4-(trifluoromethyl)-2-pyridinone, N-cyanomethyl-3-bromo-4-methyl-2-pyridinone, N-cyanomethyl-5-chloro-4-(trifluoromethylthio)-2-pyridinone, N-cyanomethyl-3-cyano-5-(difluoromethyl)-2-pyridinone, N-cyanomethyl-3-fluoro-4-(difluoromethyl)-2-pyridinone, N-cyanomethyl-5-dimethylaminocarbonyl-2-pyridinone, N-cyanomethyl-3-chloro-6-(trifluoromethyl)-2-pyridinone, N-cyanomethyl-3,5-dichloro-4-(trifluoromethyl)-2-pyridinone, N-cyanomethyl-3-nitro-5-(trifluoromethyl)-2-pyridinone, and N-cyanomethyl-3,6-difluoro-5-(trifluoromethyl)-2-pyridinone.

EXAMPLE 2

Preparation of
N-Cyanomethyl-3-fluoro-5-(trifluoromethyl-2-pyridinone

To a solution of 183 g (1.00 mole) of 2,3-di-fluoro-5-(trifluoromethyl)pyridine in 1200 ml of N-methyl-2-pyrrolidinone was added rapidly with stirring 750 ml of 10 percent aqueous sodium hydroxide. An exothermic reaction ensued. The reaction mixture was cooled in an ice bath to bring the temperature down to about 45° C., and was stirred for 0.5 hr. It was then treated with 146 g (1.22 mole) of monobromoacetonitrile dissolved in 200 ml of N-methyl-2-pyrrolidinone, and the resulting reaction mixture was stirred for another 45 minutes. The addition of 1.2 l of water resulted in the separation of a white solid, which was isolated by filtration, washed with water and dried. Another crop of a white solid separated out when the mother liquor was allowed to stand overnight. This solid was also separated by filtration and dried. The solids were combined and characterized as the desired product by infrared, nmr, and elemental (C,H,N) analysis and found to have a melting point of 141–143° C. The overall yield was 200 g (90.7 percent of theory).

The compounds N-cyanomethyl-4-(trifluoromethyl)-2-pyridinone, m.p. 134–136° C., and N-cyanomethyl-3,5-bis(trifluoromethyl)-2-pyridinone, m.p. 88–99° C., were prepared similarly and found to have compatible elemental (C,H,N) analyses and nmr and infrared spectra.

EXAMPLE 3

Preparation of 2,3-Dimethoxy-5-(trifluoromethyl)pyridine

Sodium hydride in an oil dispersion (8.0 g of 60 percent, 0.20 mol) was extracted with hexane to remove oil and suspended in 30 ml of tetrahydrofuran and to this 5.5 ml (0.14 mol) of anhydrous methanol was added dropwise with stirring. After about 10 min, 9.16 g (0.05 mol) of 2,3-difluoro-5-(trifluoromethyl)-pyridine was added. An exothermic reaction ensued which increased the temperature to about 60° C. The mixture was then heated at reflux for 6 hours and then a small amount of methanol was added. The mixture was allowed to cool and was thereafter poured onto ice. The resulting mixture was extracted several times with ether. The combined ether extracts were dried over sodium sulfate and concentrated by evaporation under reduced pressure to obtain 9.0 g (87 percent of theory) of the title compound as a white crystalline solid melting at 22°–23.5° C. The proton nmr spectrum was consistent with the assigned structure.

EXAMPLE 4

(Preparation of 3-Methoxy-5-(trifluoromethyl)-2-pyridinol 2,3-Dimethoxy-5-(trifluoromethyl)pyridine (8.8 g, 0.042 mol) was dissolved in 30 ml of glacial acetic acid, the mixture heated to 100° C. with stirring, and 14.8 ml of 48 percent aqueous hydrobromic acid (0.13 mol) added. The mixture was allowed to react for 20 min and was then poured onto ice. The solid that formed was recovered by filtration, dried, and recrystallized from ethanol to obtain 5.5 g (67 percent of theory) of the title compound as a white powder melting at 115°–117° C. The proton nmr spectrum was consistent with the assigned structure.

Anal: Calc for $C_7H_6F_3NO_2$ % C, 43.53; % H, 3.13: % N, 7.25. Found % C, 43.59; % H, 3.02; % N, 7.19.

EXAMPLE 5

(Preparation of 3-Bromo-2-methoxy-5-(trifluoromethyl)pyridine

A mixture of 7.6 g of 2-chloro-3-bromo-5-(trifluoromethyl)pyridine, 6.2 ml of 25 percent sodium methoxide in methanol (0.027 mol), and 20 ml of anhydrous methanol was prepared and allowed to react at ambient temperature with stirring for 16 hours. The mixture was then poured onto ice and the resulting mixture extracted with ether. The ether extract was extracted with water, dried over sodium sulfate, and concentrated by evaporation under reduced pressure and the residue was purified by distillation under reduced pressure to obtain 4.1 g (65 percent of theory) of the title compound as a colorless oil boiling at 86°–88° C. at 21 mm pressure and having a refractive index at 19° C. of 1.4816. The proton nmr spectrum was consistent with the assigned structure.

Anal: Calc for $C_7H_5BrF_3NO$ % C, 32.84; % H, 1.97: % N, 5.47. Found % C, 32.79; % H, 1.95: % N, 5.52.

EXAMPLE 6

Preparation of 2-Methoxy-3-methyl-5-(trifluoromethyl)pyridine

A solution of 5.12 g (0.020 mol) of 3-bromo-2-methoxy-5-(trifluoromethyl)pyridine in 60 ml of ether was cooled to −70° C. and blanketed with nitrogen. A solution containing 0.021 mole of butyl lithium (8.4 ml of 2.5 M) was added slowly with stirring keeping the temperature below about −65° C. and the mixture allowed to react for another 30 min. Methyl iodide (0.62 ml, 0.01 mol) was added to the mixture and stirring continued at −70° C. for about 30 min. The mixture was allowed to warm to about 20° C. and was then poured onto a mixture of ice and saturated aqueous ammonium chloride. The organic layer that formed was recovered. The aqueous layer was extracted with ether and the extract added to the organic layer. The combined organic materials were dried over sodium sulfate and concentrated by evaporation under reduced pressure. The residue was distilled to obtain 2.1 g (54 percent of theory) of the title compound as a colorless oil boiling at 67°–69° C. at 24 mm pressure. The proton nmr spectrum was consistent with the assigned structure.

EXAMPLE 7

Preparation of 3-Methyl-5-(trifluoromethyl)-2-pyridinol

Two ml of 48 percent hydrobromic acid were added with stirring to mixture of 1.38 g (5.5 mol) of 2-methoxy-3-methyl-5-(trifluoromethyl)pyridine and 6 ml of glacial acetic acid at 100° C. and the mixture was allowed to react at about 95° C. for 20 min. The mixture was then cooled and poured onto ice and the solid that formed was collected by filtration. A second crop of solid was obtained by adding more water to the filtrate. The combined solids were dried to obtain 0.40 g (40 percent of theory) of the title compound as a white powder melting at 141°–143° C. The proton nmr spectrum was consistent with the assigned structure.

Anal: Calc for $C_7H_6F_3NO$ % C, 47.47; % H, 3.41; % N, 7.91, Found % C, 47.18; % H, 3.35; % N, 7.80.

EXAMPLE 8

Preparation of 2-Methoxy-5-(trifluoromethyl)-3-pyridinecarboxaldehyde

A solution of 5.18 g (0.020 mol) of 3-bromo-2-methoxy-5-(trifluoromethyl)pyridine in 50 ml of ether was cooled to -100° C. and blanketed with nitrogen. A solution containing 0.024 mole of butyl lithium in hexane (15.0 ml of 1.6 M) was added slowly with stirring keeping the temperature below about −95° C. and the mixture was allowed to react for another 15 min. Dimethylformamide (7.5 ml, 0.097 mol) was added to the mixture at below −95° C. and stirring continued for about 30 min. The mixture was allowed to warm to about 20° C. and was then poured onto a mixture of ice and 1N hydrochloric acid. The mixture that formed was extracted with ether and the extract was dried over sodium sulfate and concentrated by evaporation under reduced pressure. The residue was distilled in a Kugelrohr apparatus to obtain 3.6 g (86 percent of theory) of the title compound as an oil which solidified to a white crystalline solid. The proton nmr spectrum was consistent with the assigned structure.

EXAMPLE 9

Preparation of
2-Methoxy-5-(trifluoromethyl)-3-pyridinecarboxaldehyde Oxime

A solution of 1.33 g (0.013 mol) of sodium carbonate in 15 ml of water was added with stirring to a mixture of 4.2 g (0.020 mol) of 2-methoxy-5-(trifluoromethyl-3-pyridinecarboxaldehyde and 1.74 g (0.025 mol) of hydroxylamine hydrochloride in 15 ml of water and the mixture was allowed to react for 2.5 hours at ambient temperature. It was then extracted several times with ether and the ether extracts were combined, dried over sodium sulfate, and concentrated by evaporation under reduced pressure. The residue was triturated with hot hexane, filtered, and dried to obtain 3.1 g (69 percent of theory) of the title compound as a white powder melting at 98–104° C. The proton nmr spectrum was consistent with the assigned structure. Anal: Calc for $C_8H_7F_3N_2O_2$ % C, 43.64: % H, 3.21: % N, 12.73, Found % C, 43.50; % H, 290; % N, 12.53.

EXAMPLE 10

Preparation of
3-Cyano-2-methoxy-5-(trifluoromethyl)pyridine

2-Methoxy-5-(trifluoromethyl)-3-pyridinecarboxaldehyde oxime (3.9 g, 0.018 mol) was added to a mixture of 1.9 ml (0.020 mol) of phosphorus oxychloride in 20 ml of acetonitrile and the resulting mixture heated at reflux with stirring for 1 hour. It was then allowed to cool and was poured onto ice. The mixture obtained was extracted several times with methylene chloride and the combined extracts were in turn extracted with saturated aqueous sodium chloride. The methylene chloride solution was dried over sodium sulfate and concentrated by evaporation under reduced pressure to obtain 3.2 g (89 percent of theory of the title compound as a yellow oil which solidified on standing. The proton nmr spectrum was consistent with the assigned structure.

EXAMPLE 11

Preparation of 3-Cyano-5-(trifluoromethyl)-2-pyridinol

Iodotrimethylsilane (6.2 ml, 0.044 mol) was added with stirring to a solution of 3.15 g (0.016 mol) of 3-cyano-2-methoxy-5-(trifluoromethyl)pyridine in 80 ml of chloroform under nitrogen and the mixture was allowed to stir at ambient temperature overnight. It was then concentrated by evaporation under reduced pressure and the residue partitioned between ether and 1N aqueous sodium hydroxide. The ethereal phase was extracted with more aqueous sodium hydroxide and the combined alkaline solutions were cooled and acidified with concentrated aqueous hydrochloric acid. The resulting mixture was extracted with ether several times and the combined ether extracts dried over sodium sulfate and concentrated by evaporation under reduced pressure. The residue was triturated with hot hexane, filtered, and dried to obtain 1.8 g (62 percent of theory) of the title compound as off-white crystals melting at 177–178.5° C. The proton nmr spectrum was consistent with the assigned structure.

EXAMPLE 12

Preparation of 5-Acetyl-3-cyano-6-methyl-2-pyridinol

Sodium methoxide (5.9 ml of a 25 percent solution in methanol, 0.027 mol) in 14 ml of ethanol was added with stirring to a solution of 2.28 g (0.027 mol) of cyanoacetamide in 25 ml of warm ethanol and the mixture allowed to react at ambient temperature for 24 hours. The solid that formed was collected by filtration, washed with ether, and dissolved in 60 ml of water. The aqueous solution was acidified to pH 1 with concentrated aqueous hydrochloric acid and the solids that formed were recovered by filtration and recrystallized from ethanol to obtain 2.7 g (60 percent of theory) of the title compound as pale yellow needles melting at 125–127° C. The proton nmr spectrum was consistent with the assigned structure.

Anal: Calc for $C_8H_7F_3N_2O_2$ % C, 61.36: % H, 4.58; % N, 15.90, Found % C, 61.21: % H, 4.57; % N, 15.65.

EXAMPLE 4

(Preparation of 3-Fluoro-2-methoxy-5-pyridinol

Butyl lithium (8.5 ml of 2.5 M in hexane, 21.2 mmol) was added dropwise with stirring under nitrogen to a solution of 5-bromo-3-fluoro-2-methoxypyridine (4.20 g, 20.4 mmol) in 25 ml of anhydrous ether cooling to keep the temperature below −63° C. The mixture was allowed to react for 15 min and then 2.38 ml (21.0 mmol) of trimethyl borate was added with stirring and the mixture was allowed to warm to −20° C. and stir for 1 hour. Glacial acetic acid (1.85 ml, 32.4 mmol) and then aqueous hydrogen peroxide (2.4 ml, 24 mmol) were carefully added with stirring and the mixture was allowed to react for 20 min at −5° to −20° C. The reaction mixture was then poured into saturated aqueous ferrous ammonium sulfate and the resulting mixture was extracted with 30 ml of ether. The ether extract was extracted twice with the ferrous ammonium sulfate solution and once with saturated aqueous sodium chloride and was then filtered through sodium sulfate and concentrated by evaporation under reduced pressure to obtain 2.28 g of solid material. This appeared to be a borate. It was taken up in 30 ml of 1N sodium hydroxide and treated with 4.0 ml of aqueous hydrogen peroxide and the mixture was allowed to stir at ambient temperature for 4 hours. The reaction mixture was acidified with concentrated hydrochloric acid to pH 4 and then extracted three times with 30 ml portions of methylene chloride. The combined organic extracts were filtered through sodium sulfate and concentrated by evaporation under reduced pressure to obtain 1.85 g of the title compound. This was recrystallized from a mixture of ether and hexane to obtain a purified sample. The proton nmr spectrum was consistent with the assigned structure. Anal: Calc for $C_6H_6FNO_2$ % C, 50.35; % H, 4.23: % N, 9.79, Found % C, 49.92; % H, 4.08; % N, 9.67.

EXAMPLE 15

(Preparation of
3-Fluoro-2-methoxy-5-(1,1,2,2-tetrafluoroethoxy)pyridine

3-Fluoro-2-methoxy-5-pyridinol (1.60 g, 11.2 mmol) and 0.04 g (0.7 mmol) of potassium hydroxide were added to 10 ml of dimethylformamide and the mixture blanketed with nitrogen and heated to 70° C. with stirring. An excess of tetrafluoroethylene was introduced into the liquid by means of a sparge tube. After stirring 4 hours at 70° C. no reaction was observed so another 0.04 g of potassium hydroxide was added and the tetrafluoroethylene addition continued. The reaction was indicated to be complete by F$^{19}$ nmr after 3 hours. The mixture was allowed to cool and was then poured into a mixture of 50 ml of water and 60 ml of ether. The ethereal layer was extracted with 2-25 ml portions of water and one of saturated aqueous sodium chloride and dried over sodium sulfate. The combined aqueous extracts were extracted with ether and the ethereal layer dried. The combined ethereal solutions were concentrated by evaporation under reduced pressure to obtain 1.65 g of the title compound as a yellow oil. The proton nmr spectrum was consistent with the assigned structure.

EXAMPLE 16

Preparation of 3-Fluoro-5-(1,1,2,2-tetrafluoroethoxy)-2-pyridinol

Sodium iodide (1.80 g, 12.0 mmol) and then chlorotrimethylsilane (1.5 ml, 11.8 mmol) were added to a solution of 3-fluoro-2-methoxy-5-(1,1,2,2-tetrafluoroethoxy)pyridine (1.65 g, 6.79 mmol) in 8 ml of acetonitrile with stirring and under nitrogen and the mixture was heated at reflux for 2 5 hours. It was then allowed to cool and was diluted with 20 ml of methylene chloride. The resulting solution was extracted with water and with saturated aqueous sodium hydroxide, dried over sodium sulfate, and concentrated by evaporation under reduced pressure to obtain the title compound as a solid. This was recrystallized from toluene to obtain 0.95 g of the product as a white solid. The proton nmr spectrum was consistent with the assigned structure.

Anal: Calc for $C_7H_4F_5NO_2$ % C, 36.70; % H, 1.76; % N, 6.11, Found % C, 37.13; % H, 1.68: % N, 5.93.

EXAMPLE 17

Preparation of N-Cyanomethyl-3-fluoro-5-(1,1,2,2-tetrafluoroethoxy)-2-pyridinone Diisopropylethylamine (0.82 ml, 4.7 mmol) and 0.30 ml (4.3 mmol) of bromoacetonitrile were added consecutively with stirring at ambient temperature to 3-fluoro-5-(1,1.2,2-tetrafluoroethoxy)-2-pyridinol (0.90 g, 3.98 mmol) in 5 ml of methylene chloride and the mixture allowed to react overnight. It was then diluted with 25 ml of methylene chloride, extracted with 25 ml of water and with dilute aqueous sodium carbonate, dried over sodium sulfate, and concentrated by evaporation under reduced pressure to obtain the title compound as a solid. This was recrystallized from toluene to obtain 0.92 g (86 percent of theory) of purified material melting at 75.5–77° C. The proton nmr spectrum was consistent with the assigned structure.

Anal: Calc for $C_9H_5F_5N_2O_2$ % C, 40.31; % H, 1.88: % N, 10.45, Found % C, 40.28; % H, 1.85; % N, 10.17.

EXAMPLE 18

Control of Aster Leafhopper by Systemic Action

Rice seedlings grown on vermiculite substrate were removed from the vermiculite and placed in 15 ml of 10 percent Hoagland's solution in 1 oz. plastic pill cups. Aqueous acetone solutions containing predetermined concentrations of the test compounds were prepared and 5 ml injected into each cup. A clear plastic tube was then placed over each plant (and its cup). Ten adult, aster leafhoppers (*Macrosteles severni*) were placed within each tube and each tube was covered with a screen cap. Mortality was determined after 3 days. Some of the compounds tested that were active at 200 ppm concentration (in the cup) and the results obtained at this dose are given in the following table.

| W | X | Y | Z | Mortality, percent |
|---|---|---|---|---|
| H | CF$_3$ | H | F | 100 |
| H | CF$_3$ | H | Cl | 100 |
| H | CF$_3$ | H | I | 100 |
| H | CF$_3$ | H | H | 100 |
| H | CF$_3$ | H | CH$_3$ | 100 |
| H | CF$_3$ | H | SCH$_3$ | 60 |
| H | CF$_3$ | H | CN | 100 |
| H | Cl | H | F | 98 |
| H | Br | H | F | 100 |
| H | Cl | H | Cl | 44 |
| H | Br | H | Br | 24 |
| H | Cl | H | H | 77 |
| H | Br | H | H | 55 |
| H | I | H | F | 100 |
| H | CO$_2$C$_2$H$_5$ | H | F | 100 |
| H | CO$_2$CH(CH$_3$)$_2$ | H | F | 90 |
| H | OCF$_2$CF$_2$H | H | F | 70 |
| H | H | H | CN | 100 |

EXAMPLE 19

Control of Insects by Contact and Systemic Action

Aster leafhopper, greenhouse whitefly, and 2-spotted spider mite control by selected compounds was determined. Rice seedlings grown on vermiculite substrate were removed from the vermiculite and placed in 10 percent Hoagland's solution in 1 oz. plastic pill cups. Suspensions or solutions of the test compounds in aqueous acetone containing a surfactant were prepared and sprayed onto the plants. The foliage was allowed to dry and then a clear plastic tube was placed over each plant (and its cup). Ten adult aster leafhoppers (*Macrosteles severni*) were placed inside each tube and each tube was covered with a screen cap. Mortality was determined after three days.

Cotton seedlings, approximately two weeks old and growing individually in 3 inch pots, were trimmed to the first true leaf and infested with adult whiteflies (*Trialeuroides vaporarium*). Oviposition was allowed to take place for 2–3 days; and the plants were then moved to a greenhouse and held for 5 days during which time most of the eggs hatched. The plants were then sprayed with predetermined concentrations of test compounds in aqueous acetone containing a surfactant and were held in a greenhouse. The degree of control was determined after 9–10 days.

Cotton seedlings approximately 2 weeks old and growing individually in 3 inch pots were trimmed to the first true leaf and infested with 50–100 2-spotted spider mites. The leaf of each plant was then dipped into an aqueous acetone mixture containing a surfactant and a predetermined concentration of a test compound and 25 ml of the mixture were poured into the pot containing the cotton plant. The plants were placed in a greenhouse and mortality was determined 5 days after treatment. The control was corrected for any natural mortality in the untreated checks.

Some of the active compounds employed, the rates used, and the results obtained in the above tests are given in the following table.

| W | X | Y | Z | Rate, ppm | Aster Leaf-hopper Contact | White-fly | 2-Spotted Spider Mite |
|---|---|---|---|---|---|---|---|
| H | CF$_3$ | H | F | 25 | 100 | NT | NT |
| H | CF$_3$ | H | Cl | 800 | 100 | 100 | 0 |
| H | CF$_3$ | H | Cl | 25 | 100 | NT | NT |
| H | CF$_3$ | H | I | 800 | 100 | NT | NT |
| H | CF$_3$ | H | I | 25 | 90 | NT | NT |
| H | CF$_3$ | H | H | 800 | 100 | 100 | 90 |
| H | CF$_3$ | H | CH$_3$ | 800 | 70 | NT | NT |
| H | Cl | H | F | 800 | 100 | 0 | NT |
| H | Br | H | F | 800 | 100 | 100 | 0 |
| H | Cl | H | H | 800 | NT | 95 | 83 |
| H | I | H | F | 800 | 100 | NT | NT |
| H | OCF$_2$CF$_2$H | H | F | 800 | 50 | NT | NT |

NT means no test

EXAMPLE 20

Control of Tobacco Budworm by Injection

Test compounds were dissolved in dimethyl sulfoxide to prepare test solutions containing specific known concentrations. A group of 5 to 10 tobacco budworm (*Heliothis virescens*) larvae in the 3rd to 4th instar stage (weighing about 50-60 mg each) were injected with 0.5 ml of test solution near the anus along the dorsal midline and then placed individually in petri dishes containing a pinto bean diet. After 24 hours mortality was determined using ability to right as the criterion for death. Some of the active compounds tested, dose rates employed, and results obtained are recorded in the following table.

| W | X | Y | Z | Dose μg/Worm | Percent Mortality |
|---|---|---|---|---|---|
| H | CF$_3$ | H | H | 50 | 95 |
| H | CF$_3$ | H | F | 25 | 100 |
| H | CF$_3$ | H | Cl | 50 | 80 |
| H | CF$_3$ | H | Br | 50 | 80 |
| H | CF$_3$ | H | I | 50 | 70 |
| H | CF$_3$ | H | CN | 50 | 80 |
| H | CF$_3$ | H | CF$_3$ | 50 | 70 |
| H | CF$_3$ | H | OC$_6$H$_5$ | 50 | 60 |
| H | CO$_2$CH(CH$_3$)$_2$ | H | F | 50 | 70 |
| CH$_3$ | CH$_3$CO | H | CN | 50 | 40 |
| H | Cl | H | Cl | 50 | 40 |
| H | Br | H | Br | 50 | 40 |
| H | Br | H | H | 50 | 60 |
| H | CH$_3$ | H | H | 50 | 50 |
| Cl | Cl | H | Cl | 50 | 80 |
| H | Cl | CF$_3$ | H | 50 | 40 |
| H | H | H | CN | 50 | 60 |
| H | H | H | Br | 50 | 40 |

What is claimed is:

1. An N-cyanomethyl-2-pyridinone compound of the Formula

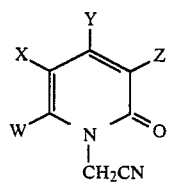

wherein
W represents H, F, Cl, CH$_3$, or CF$_3$;
X represents H, F, Cl, Br, I, R, OR, OPh, SR, CF$_2$Cl, CN, COR, CO$_2$R', or CONR'R';
Y represents H, R, OR, SR, or OPh:
Z represents H, F, Cl, Br, I, R, OR, SR, OPh, NO$_2$, or CN;
R represents C$_1$-C$_3$ alkyl or C$_1$-C$_3$ alkyl partially or totally substituted with fluorine:
R' represents C$_1$-C$_4$ alkyl:
with the proviso that at least one of W, X, Y, and Z represents other than H.

2. A compound of claim 1 wherein W represents H.
3. A compound of claim 1 wherein X represents Cl, Br, I, CF$_3$, CF$_2$H, C$_2$F$_5$, CN, or CO$_2$R'.
4. A compound of claim 1 wherein Y represents H.
5. A compound of claim 1 wherein Z represents H, F, Cl, or CN.
6. A compound of claim 1 wherein W represents H; X represents Cl, Br, I, CF$_3$, CF$_2$H, C$_2$F$_5$, CN, or CO$_2$R'; Y represents H: and Z represents H, F, Cl, or CN.
7. A compound of claim 6 wherein X represents CF$_3$.
8. A compound of claim 1 wherein X represents CF$_3$.
9. The compound of claim 8 N-cyanomethyl-3-fluoro-5-(trifluoromethyl)-2-pyridinone.
10. The compound of claim 8 N-cyanomethyl-3-chloro-5-(trifluoromethyl)-2-pyridinone.
11. The compound of claim 8 N-cyanomethyl-3-cyano-5-(trifluoromethyl)-2-pyridinone.
12. A composition which comprises an insecticidal amount of a compound of claim 1 in combination with at least one agricultural adjuvant or carrier.
13. A composition which comprises an insecticidal amount of a compound of claim 2 in combination with at least one agricultural adjuvant or carrier.
14. A composition which comprises an insecticidal amount of a compound of claim 3 in combination with at least one agricultural adjuvant or carrier.
15. A composition which comprises an insecticidal amount of a compound of claim 4 in combination with at least one agricultural adjuvant or carrier.
16. A composition which comprises an insecticidal amount of a compound of claim 5 in combination with at least one agricultural adjuvant or carrier.
17. A composition which comprises an insecticidal amount of a compound of claim 6 in combination with at least one agricultural adjuvant or carrier.
18. A composition which comprises an insecticidal amount of a compound of claim 7 in combination with at least one agricultural adjuvant or carrier.
19. A composition which comprises an insecticidal amount of a compound of claim 8 in combination with at least one agricultural adjuvant or carrier.
20. A composition which comprises an insecticidal amount of a compound of claim 9 in combination with at least one agricultural adjuvant or carrier.
21. A composition which comprises an insecticidal amount of a compound of claim 10 in combination with at least one agricultural adjuvant or carrier.
22. A composition which comprises an insecticidal amount of a compound of claim 11 in combination with at least one agricultural adjuvant or carrier.
23. A method of controlling insects which comprises contacting said insects, the locus of said insects, or the plants upon which said insects feed with an insecticidal amount of a compound of the Formula

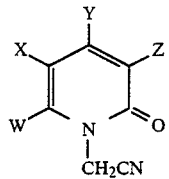

wherein
 W represents H, F, Cl, CH₃, or CF₃;
 X represents H, F, Cl, Br, I, R, OR, OPh, SR, CF₂Cl, CN, COR, CO₂R', or CONR'R';
 Y represents H, R, OR, SR, OR, or OPh;
 Z represents H, F, Cl, Br, I, R, OR, SR, OPh, NO₂, or CN;
 R represents C₁-C₃ alkyl or C₁-C₃ alkyl partially or totally substituted with fluorine;
 R' represents C₁-C₄ alkyl;
 with the proviso that at least one of W, X, Y, and Z represents other than H.

24. A method of claim 23 wherein W represents H.

25. A method of claim 23 wherein X represents Cl, Br, I, CF₃, CF₂H, C₂F₅, CN, or CO₂R'.

26. A method of claim 23 wherein Y represents H.

27. A method of claim 23 wherein Z represents H, F, Cl, or CN.

28. A method of claim 23 wherein W represents H; X represents Cl, Br, I, CF₃, CF₂H, C₂F₅, CN, or CO₂R'; Y represents H; and Z represents H, F, Cl, or CN.

29. A method of claim 28 wherein X represents CF₃.

30. A method of claim 23 wherein X represents CF₃.

31. The method of claim 29 wherein the compound is N-cyanomethyl-3-fluoro-5-(trifluoromethyl)-2-pyridinone.

32. The method of claim 29 wherein the compound is N-cyanomethyl-3-chloro-5-(trifluoromethyl)-2-pyridinone.

33. The method of claim 29 wherein the compound is N-cyanomethyl-3-cyano-5-(trifluoromethyl)-2-pyridinone.

34. A method of claim 23 wherein the plants contacted are rice.

35. A method of claim 17 wherein the insects are leafhoppers or planthoppers.

36. A method of claim 28 wherein the insects are leafhoppers or planthoppers.

37. A method of claim 31 wherein the insects are leafhoppers or planthoppers.

38. A method of claim 32 wherein the insects are leafhoppers or planthoppers.

39. A method of claim 33 wherein the insects are leafhoppers or planthoppers.

* * * * *